(12) United States Patent
Jacob et al.

(10) Patent No.: US 9,119,788 B2
(45) Date of Patent: Sep. 1, 2015

(54) METHOD FOR PRODUCTION OF PARTICLES OF PHARMACEUTICAL SUBSTANCES AND THE USE THEREOF

(71) Applicant: GLATT GMBH, Binzen (DE)

(72) Inventors: Michael Jacob, Weimar (DE); Annette Grave, Loerrach (DE); Reinhard Nowak, Binzen (DE)

(73) Assignee: GLATT GMBH, Binzen (DE)

( * ) Notice: Subject to any disclaimer, the term of this patent is extended or adjusted under 35 U.S.C. 154(b) by 0 days.

(21) Appl. No.: 14/068,197

(22) Filed: Oct. 31, 2013

(65) Prior Publication Data

US 2014/0054808 A1 Feb. 27, 2014

Related U.S. Application Data

(62) Division of application No. 11/990,107, filed as application No. PCT/EP2006/007848 on Aug. 8, 2006, now Pat. No. 8,597,685.

(51) Int. Cl.
| | | |
|---|---|---|
| *A61K 31/192* | (2006.01) | |
| *A61K 9/14* | (2006.01) | |
| *B01J 2/04* | (2006.01) | |
| *A61K 9/16* | (2006.01) | |
| *B01J 2/16* | (2006.01) | |

(52) U.S. Cl.
CPC ............... *A61K 9/1688* (2013.01); *A61K 9/167* (2013.01); *A61K 31/192* (2013.01); *B01J 2/16* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 3,231,413 A | | 1/1966 | Yves |
| 3,382,093 A | | 5/1968 | Nack |
| 4,086,346 A | | 4/1978 | Bocker et al. |
| 4,092,089 A | | 5/1978 | Bocker et al. |
| 4,895,733 A | * | 1/1990 | Imanidis et al. ............... 427/8 |
| 5,320,855 A | | 6/1994 | Roche et al. |
| 6,322,816 B1 | | 11/2001 | Zeidler et al. |
| 6,514,489 B1 | | 2/2003 | Shacknai et al. |
| 2003/0203026 A1 | | 10/2003 | Sherry et al. |
| 2004/0228978 A1 | * | 11/2004 | Jacob et al. ............... 427/430.1 |
| 2005/0003000 A1 | | 1/2005 | Einig et al. |

FOREIGN PATENT DOCUMENTS

| | | |
|---|---|---|
| DE | 100 04 939 | 8/2001 |
| DE | 103 22 062 | 12/2004 |
| EP | 0 230 322 | 7/1987 |
| EP | 0 241 126 | 10/1987 |
| EP | 0 250 648 | 1/1988 |
| EP | 0 290 168 | 11/1988 |
| EP | 0305356 | 3/1989 |
| EP | 0362 728 | 9/1989 |
| EP | 0 362 731 | 4/1990 |
| EP | 0362731 A2 * | 4/1999 |
| WO | WO 94/10993 | 5/1994 |
| WO | WO 96/31197 | 10/1996 |
| WO | WO 02/07706 | 1/2002 |
| WO | WO 2004/108911 | 12/2004 |
| WO | WO 2005123042 | 12/2005 |

OTHER PUBLICATIONS

Rittner (EP 0362731) Machine translation.*
International Search Report dated Feb. 5, 2007.

* cited by examiner

*Primary Examiner* — H. Sarah Park

(74) *Attorney, Agent, or Firm* — Frommer Lawrence & Haug LLP

(57) ABSTRACT

The invention relates to a method for producing particles with a length-width ratio of less than about 1.4 from a pharmaceutical substance, which method includes the following stages, that is: (a) provision of a melt of the pharmaceutical substance; (b) production of droplets of the melt by spraying into a processing chamber; (c) repeated guiding of solid particles past sprayed droplets in the processing chamber with the aid of a process gas jet which is guided in a defined way and whose temperature is fixed, depending on the solidification point of the melt, so that at least some of the droplets come into contact with particles and solidify thereon; (d) removal of particles from the processing chamber as a function of the particle size. The invention further relates to particles of pharmaceutical substances and the use thereof.

13 Claims, 1 Drawing Sheet

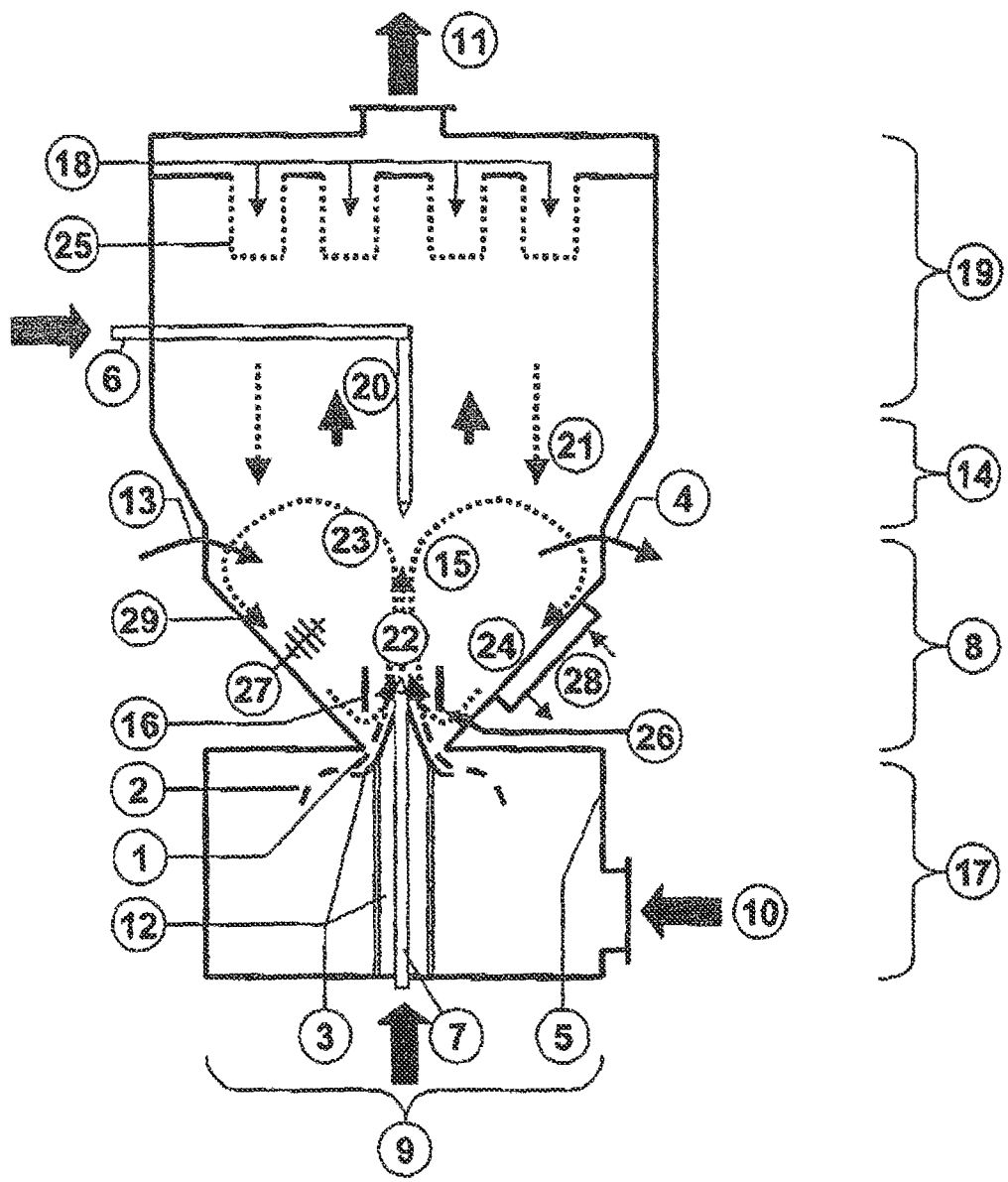

METHOD FOR PRODUCTION OF PARTICLES OF PHARMACEUTICAL SUBSTANCES AND THE USE THEREOF

The present application is a divisional of U.S. patent application Ser. No. 11/990,107 filed on Apr. 4, 2008, which claims priority from PCT patent application No. PCT/EP2006/007848 filed on Aug. 8, 2006, which claims priority from German Patent Application No. DE 10 2005 037 630.4 filed on Aug. 9, 2005, the disclosures of which are incorporated herein by reference in their entirety.

FIELD OF THE INVENTION

The invention relates to a method for producing particles from a melt, to the particles themselves, and to the use thereof. The particles are formed from pharmaceutical substances (medicinal substances and/or excipients).

BACKGROUND OF THE INVENTION

Fine-particle forms of pharmaceutical substances such as fine powders are frequently associated with technical processing disadvantages. In order to avoid such disadvantages, frequently coarser particles (granules) are provided.

Such particles of pharmaceutical substances can be used to produce dosage forms by for example compressing them alone or together with further components to give tablets. Medicinal substance-containing particles may additionally be used packed into capsules or in the form of a powder for a suspension or solution.

A number of methods are known for producing particles. Solvents are employed in some of the methods. This is disadvantageous because the solvents must be removed again during the method. Even small amounts of remaining solvents may impair the product quality. Organic solvents are additionally undesired from the viewpoint of safety at work and environmental protection.

Solidified melt granules (melt granules) are known as alternative. They are produced by melting and shock solidification, by casting and comminuting or by spray congealing in spray towers. These known methods are, however, associated with disadvantages.

Methods in which a solidified melt is comminuted are rather elaborate because they require stages of melting, solidifying and comminuting separately, for each of which different types of apparatuses are required. In addition, it is rather difficult to obtain particulate material with a particle size distribution. Moreover, the particles obtained by comminution have irregular shapes, thus making further handling difficult.

The production of melt granules by solidifying a melt in a spray tower is also associated with disadvantages. There is typically formation of a relatively large proportion of material of unwanted particle size, which must be separated off and remelted. The resulting particles are ordinarily not uniformly globular, thus impairing their handling properties.

A method of the last-mentioned type is described in EP 0 362 731. The method is carried out by atomizing an active pharmaceutical ingredient melt in a spray chilling tower in order to produce active pharmaceutical ingredient particles. Ibuprofen is employed for example as active ingredient. The particles are obtained by cooling droplets of a melt which is atomized in a spray chilling tower in the presence of crystallization nuclei and is brought into contact with a chilling gas. Desired particles are removed with the aid of a sieve from the powder which is formed.

A number of other patents and patent applications also relate to the production of medicinal substance particles, specifically of ibuprofen particles, and to the use thereof for producing certain dosage forms.

EP 0 362 728 A2 relates to a method for obtaining ibuprofen for direct tableting. In this case, an ibuprofen melt is solidified on a contact-chilling apparatus and then comminuted. Since the production of the particles takes place in two stages, the method is rather elaborate. In addition, the particles have irregular shapes owing to the comminution process.

U.S. Pat. No. 6,322,816 relates to analgesic products with rapid release of active ingredient. A suitable active ingredient is in particular ibuprofen. The active ingredient is present in a special adjuvant matrix.

US 2003/0203026 relates to therapeutic agents, in particular a compressed tablet. This contains a granular component which comprises a plurality of solidified melt granules of a non-steroidal anti-inflammatory drug which has a melting point in the range from 30 to 200° C., and a disintegant uniformly distributed therein. Ibuprofen is a preferred active ingredient. The melt can be solidified by chilling and then comminuted. Alternatively, the melt can be sprayed through a nozzle in order to make it possible to solidify the material, which is then collected.

US 2005/0003000 relates to a method for forming ibuprofen solids, where additives are added to a solution of ibuprofen and are removed again later.

WO 02/07706 relates to a method for coating solid particles, for example ibuprofen particles. This document is not concerned with the production of these particles employed as starting material.

WO 94/10993 relates to pharmaceutical formulations of ibuprofen. The production of a particulate dosage form is described inter alia, there being provision for addition of an aqueous solution of a binding to ibuprofen.

U.S. Pat. No. 5,320,855 relates to chewable tablets which are produced from granules of a medicament. The granules in turn are produced by rotogranulation of a mixture of a medicinal substance such as ibuprofen and excipients and is provided with particular coatings.

EP 0 290 168 relates to an ibuprofen tablet with sustained release. There is provided in particular an ibuprofen-containing matrix which is obtained by granulating ibuprofen mixed with excipients in powder form using a particular solution as granulation liquid.

EP 0 241 126 relates to a solid pharmaceutical composition which includes granules which consist essentially of an aggregate of ibuprofen crystals. The method generally includes the compaction of crystalline ibuprofen in order to bring about aggregation of the crystalline ibuprofen to form an aggregate material, the comminution of the aggregate material and the selection of granules with the desired size. It is possible for example to produce crystalline ibuprofen by wetting with a solvent. An extrusion then takes place. The granules obtained in this case are dried.

EP 0 230 322 relates to a pharmaceutical composition with sustained release of the active ingredient. Sugar esthers of higher fatty acids are employed in this case. The production method includes mixing and granulating components.

EP 0 250 648 relates to a pharmaceutical product for sustained release of ibuprofen. The product is in the form of tablets which comprise the active ingredient in microspheres. Production takes place by mixing the ibuprofen and a binding to give a homogeneous mixture and moistening with water. The mixture is then shaped to microspheres by extrusion, and tablets are finally produced therefrom.

WO 96/31197 relates to homogeneous mixtures of low-melting medicinal substances and additives for controlled release. One method for producing such a formulation includes the melting of a medicinal substance and an additive at a temperature below 150° C., mixing the medicinal substance and the additive to form a homogeneous mixture, and finally hardening the homogeneous mixture to form a medicinal substance-additive composite material. It is intended to introduce the molten mass into capsules, where it then hardens on cooling.

The prior art further includes proposals for producing granules by using spouted bed apparatuses. Thus, DE 103 22 062 A1 discloses the production of granules from various materials by applying liquids in a solid stream in a spouted bed apparatus. Said application is, however, not concerned either with the specifics of pharmaceutical substances or with the conditions which must be observed when producing particles from a melt.

DE 100 04 939 C1 relates to a controllable gas stream unit for spouted bed apparatuses. The patent is not concerned with the production of melt granules.

WO 2004/108911 A2 relates to methods for producing enzyme granules and to such granules. A spouted bed apparatus is employed for the production. The application is not concerned with melt granules.

OBJECTS AND BRIEF DESCRIPTION OF THE INVENTION

One object of the present invention is to indicate a method with which preferably globular particles of pharmaceutical substances (medicinal substances and/or excipients) can be produced from a melt. It is intended in this connection to be able to avoid the disadvantages of conventional methods. A further object is to produce preferably globular particles and collections of such particles and to make it possible for them to be used for producing pharmaceutical dosage forms.

It has been found according to the invention that it is possible to build up essentially globular particles from single droplets of a melt when the droplets are guided with the aid of a process gas at a suitable temperature so that particles of melt which has already solidified can come into contact with droplets anew. A difference from the production of particles from a melt in a conventional spray tower is that the particles which form are circulated in a suitable processing chamber until they have reached the desired size through repeated addition of droplets of the melt.

Accordingly, the invention provides a method for producing particles with a length-width ratio of less than about 1.4 from a pharmaceutical substance, which method includes the following stages:

(a) provision of a melt of the pharmaceutical substance;
(b) production of droplets of the melt by spraying into a processing chamber;
(c) repeated guiding of solid particles past sprayed droplets in the processing chamber with the aid of a process gas jet which is guided in a defined way and whose temperature is fixed, depending on the solidification point of the melt, so that at least some of the droplets come into contact with particles and solidify thereon;
(d) removal of particles from the processing chamber as a function of the particle size.

The invention also provides particles of a pharmaceutical substance where the particles have an average particle size of from 0.1 to 3 mm and a length-width ratio of less than about 1.4, and are produced from a melt of the pharmaceutical substance.

BRIEF DESCRIPTION OF THE FIGURE

The invention is explained in more detail below with reference to a FIGURE. This FIGURE depicts diagrammatically a system for carrying out the method of the invention.

DETAILED DESCRIPTION OF THE INVENTION

Definitions

Some technical terms used in the description and in the claims are explained below.

A melt is produced by melting a substance with heating to a temperature which is typically in the range from 30° C. to 300° C. The melt is preferably obtained by complete melting of a substance or mixture of substances, so that a homogeneous phase is formed. Alternatively, solid substances can be dispersed in the melt. Unless indicated otherwise, the term melt is understood here in this wider sense.

The expression "pharmaceutical substance" is intended to refer to medicinal substances, pharmaceutical excipients and mixtures of such components. In a preferred embodiment, the pharmaceutical substance is a medicinal substance.

Since it is intended according to the invention to produce particles from pharmaceutical substances by melt granulation, it is further necessary for the substances to be meltable without substantial decomposition, that is to say without impairing their pharmaceutical use. Substances which undergo decomposition on melting cannot be processed according to the invention unless the melting point can be reduced by suitable additions to make the melting and processing possible. A person skilled in the art is able to establish by tests whether the quality is still sufficient after the melting and solidification. Tests for ensuring the quality of numerous pharmaceutical substances are laid down in the appropriate pharmacopoeias.

Examples of medicinal substances which can be processed by melt granulation are divalproex sodium, ibuprofen, ramipril, dibenzyline, erythrityl tetranitrate, isosorbide dinitrate, methosuximide, ketoprofen, gemfibrozil, paroxetine hydrochloride and trimipramine maleate. A medicinal substance which is preferred according to the invention is ibuprofen.

Examples of pharmaceutical excipients are low-melting binders, for example gelatine and starch compositions, and low-melting insoluble polymers.

A particle is referred to as globular according to the invention if the length-width ratio (meaning the ratio of the length (largest dimension) of the particle divided by the width (smallest dimension) which is fixed at an angle of 90" in relation to the length) is less than about 1.4. The length-width ratio of a globular particle is preferably less than about 1.3, more preferably less than about 1.2, even more preferably less than about 1.1 and in particular less than about 1.05.

The particles are additionally characterized by their size. The particle size distribution can be determined by sieve analysis. Unless indicated otherwise, the particle size refers to the weight average.

The present invention also relates to a product which comprises a plurality of particles. A product of this type comprises a collection of particles, typically 50 or more, preferably 100 or more, particles. A product of the invention comprises predominantly particles satisfying the particle criteria of the invention. Preferably at least 90%, in particular at least 95% and very particularly preferably at least 98% of the particles have a length-width ratio of less than about 1.4, preferably less than about 1.3, more preferably less than about 1.2, even more preferably less than about 1.1 and in particular less than about 1.05.

A process gas jet is utilized according to the invention to guide solid particles repeatedly past sprayed droplets. The process gas may be for example air or an inert gas such as nitrogen, carbon dioxide or a noble gas.

Preferred Embodiments

As explained above, it has been found according to the invention that it is possible to produce globular particles from single droplets of a melt. The particles preferably have a compact structure. It is further preferred for the particles to have a homogeneous surface structure. It is essential in this connection that the build up of globular particles is made possible by particles which have been introduced or formed from the melt repeatedly coming into contact with droplets of the melt, so that globular particles of a desired size can be built up. For this purpose, the particles are moved inside a processing chamber with the aid of a process gas jet guided in a defined way. Particles which have reached a desired size can leave the processing chamber.

The process gas jet is essential both for transport of matter and for transport of heat. The invention achieves, through choice of the temperature of the process gas jet as a function of the solidification point of the melt, contact being made between the sprayed droplets and particles which have already solidified to form substantially globular particles. In particular, the temperature conditions provided in the processing chamber are such as to sufficiently delay solidification in order to make it possible for the particles which are already solid to be wetted with the sprayed droplets of the melt and for globular structures to form. On the other hand, the coming into contact with one another, and adhesion, of particles with a liquid surface is substantially prevented according to the invention.

Accordingly, the process gas jet has a temperature which is below the solidification product of the melt. On the other hand, the temperature of the process gas jet must not permit immediate solidification of droplets sprayed into the processing chamber. The temperature of the process gas jet is preferably 10° C. to 40° C. below the solidification point of the melt.

It is preferred according the invention for droplets of the melt and solid particles to be brought into contact with one another in a spouted bed. Spouted bed means that the completely fluidized solid particles are located in a closed solid flow which is stable over time. The spouted bed is generated with the aid of the process gas jet which is guided in a defined way. Three fluidization states or zones are to be distinguished within the spouted bed. In a first zone or ejection zone, the solid particles are accelerated through the action of the process gas jet which is guided in a defined way, and the particles in this zone move in the direction of flow of the process gas jet. Typically, the process gas jet is guided vertically upwards. Correspondingly, the flow prevailing in the ejection zone of the spouted bed is directed vertically upwards. In a subsequent second zone or fountain zone, the particles change their direction of flow. The prevailing flow is transverse. Finally, the particles reach a third zone or return zone. The particles therein then show a motion in the opposite direction until they finally return to the inflow of the gas flow which is guided in a defined way, and are again entrained by the latter in the first zone. The particles move in the return zone typically under the influence of gravity.

The melt can be sprayed through two- or multi-fluid nozzles. A further possibility is to use pressurized nozzles for the spraying. Alternatively, droplet formation is possible by rotary atomizers, jet cutters, ultrasonic droplet formers and other devices known to the skilled person.

It is possible according to the invention, by spraying droplets of a melt into the processing chamber and allowing these droplets to solidify, to form nuclei of solid particles which are then brought into contact with further droplets in order to form particles of the desired size. An alternative or additional possibility in the method is to supply solid particles from outside. For example, undersized particles which have been removed from the process can be returned as nucleus material to the processing chamber. It is likewise possible for oversized particles which have been removed from the process, or agglomerates of particles, to be comminuted by any desired comminuting unit and returned as nucleus material to the processing chamber. It is also possible to supply particles of different compositions than that of the melt. Melt embedding of the supplied particles is possible in this way.

The particles formed by the method of the invention are removed from the processing chamber. The discharge of the finished product material from the processing chamber or a transport of material into a further downstream processing chamber can take place in the region of the transition from the transverse flow to the downwardly directed solid flow. In one embodiment, the particles discharged from the processing chamber are not classified. In another embodiment, the particles discharged from the processing chamber are removed in a classified manner through one or more screening apparatuses.

The method of the invention can be carried out for example with the aid of a device as described in DE 103 22 062 A1. The content of the application is incorporated in the present application by reference.

The method of the invention is preferably carried out using a device as shown in the appended FIGURE. This is explained in detail below.

The amount of process gas 10 (usually heated air) necessary for solidifying the particles to be produced is supplied to an inlet air chamber 17 with rectangular cross section 9 and limiting side walls 5. The process gas 10 is distributed in the inlet air chamber 17 and enters the processing chamber 8 in the form of gas jets 2 through slit apertures 1. The process gas stream which preferably enters the slit 1 horizontally is deflected by the deflecting part 3 preferably upwards into the processing chamber 8 and flows as a type of free jet into the apparatus. Thereafter it is optionally possible for the cross section of the apparatus to become larger in the expansion zone 14 so that the velocity of the process gas flow steadily diminishes upwards. The gas leaves the apparatus as exit gas 11 above the expansion zone 14 over the exit-air part 19 into which it is optionally possible for a dust-removal system (e.g. filter cartridges or textile filter elements) to be integrated.

Present in the processing chamber 8 is an amount of particles which are carried upwards by the process gas jet. In the upper region of the processing chamber 8, and in the expansion zone 14 located above it, the gas velocity decreases, so that the upward-flowing particles leave the gas jet 23 laterally and fall back into the processing chamber 8. The processing chamber 8 is limited in the lower region by inclined side walls 29. Owing to this inclination at the sides, the particles are conveyed under the action of gravity via the return zone 24 in the direction of the gas-inlet slit 1, where they are subsequently carried by the process gas back into the processing chamber 8.

This mechanism results in formation of a very uniform solid circulation 15 consisting of an upward flow and a return in the direction of the process gas inlet. This results in a high particle density in the core zone above the deflecting part 3 even when there are very small amounts of particles in the processing chamber 8. One or more spray nozzles 7 are disposed in this region and spray upwards in the same direction as the process gas jet and serve to introduce the melt.

The high particle loading in the core zone results in very advantageous conditions for heat and material transfer in the nozzle-spraying zone 22. A further consequence is that the melt is very substantially deposited on the particles and thus wets them uniformly on the particle surfaces. The uniform wetting with, at the same time, high solid circulation between nozzle-spraying region and return zone 24 has the effect that a very uniform liquid film is formed. The melt solidifies through the solidification process, and the solid remains on the particle surface. This results in very uniform and homogeneous growth of the granules, leading to a very narrow particle size distribution and a homogeneous particle structure.

The process gas may discharge some of the particles, and fines and dust, as solid-loaded exit air 20 from the processing chamber 8. Deposition of these particles is possible by using the filter system which is optionally integrated in the exit-air part 19, or the dust-removal systems downstream of the apparatus. In the case of an integrated dust-removal system 25, for example, compressed air pulses 18 can be used in order to return the retained particles as removed solid 21 into the processing chamber 8.

Compared with fluidized bed apparatuses with integrated filter systems, the dust recycling is facilitated by the upwards-directed process gas flow being substantially spatially restricted and thus the particles which are to be returned are able reliably to descend outside the gas jet. This mechanism is additionally promoted by the suction effect in the vicinity of the gas-inlet slit 1. Alternatively, particles deposited from the exit air can be returned to the processing chamber 8. For this purpose, various types of feed 26 can be disposed in the lower region of the inclined side walls 29. Owing to the high velocity of the process gas jet in the vicinity of the gas-inlet slit 1, the fine particles are sucked up and supplied to the nozzle-spraying zone 22 where they are wetted with melt and take part in the growth process.

Optionally incorporated guide plates 16 assist the gas jet, enhance the suction effect and improve the feeding of solids into the nozzle-spraying zone 22. Any agglomeration effects which occur are minimized because very high flow velocities and thus greater separation forces than in fluidized beds occur in the nozzle-spraying region. This results in the particles being separated and growing into granules with a globular shape.

The flow profile of the process gas in the processing chamber 8 has the further effect that fine particles returned from the optionally integrated filter system into the processing chamber do not fall back into the nozzle-spraying zone 22. Adhesion of fine particles and consequent agglomeration processes are suppressed thereby.

To carry out the process continuously, the apparatus can optionally be equipped with various input systems 13 for solids. It is possible thereby to supply to the process for example particles which can be obtained by comminuting for example (oversized) granules or/and consist of undersized granules. These particles then serve as granulation nuclei or as initial charge to shorten the operating time. It is additionally possible here for additives which are to be incorporated in the granules to be fed in solid form into the process.

The apparatus can further be provided with discharge elements 4 in order to be able to remove particles from the processing chamber 8. This can take place for example by an overflow or by a volumetric discharge element (e.g. a star wheel discharger) or else by a gravity separator (e.g. a zigzag classifier or an ascending pipe classifier supplied with screening gas).

It is optionally possible to attach mechanical units 27 in the processing chamber 8, but preferably in the region of the return zone 24 on the inclined walls, in order to generate, by comminution, sufficient fine material as nuclei for the granulation process. The return zone 24 can further optionally be used for siting heating devices or other heat-transfer units 28. For example, the apparatus wall can be jacketed in order to use it for example for heating or cooling the walls by employing liquid or gaseous heat transfer agents. It is thus possible to adjust optimal surface temperatures in order to avoid for example deposits of product.

Spray nozzles 6 which preferably spray downwards, but also partly upwards, can optionally be disposed in the processing chamber 8 or in the parts of the apparatus located above, the expansion zone 14 and the exit-air part 19. The liquid formulation can be sprayed in here likewise in order, for example, to produce granulation nuclei by spray drying/spray congealing in the apparatus. Alternatively, additives or other components in liquid form can be sprayed in through some of the spray units 6 and 7 and thus be incorporated homogeneously into the granular structure. If the spray nozzles 7 pass through the heated inlet air chamber 17, it is optionally possible for the liquid-carrying parts to be provided with insulators or various cooling or heating systems 12 in order to diminish damage to the liquid formulation.

A further advantage of the process of the invention which should be mentioned is the very simple configuration which combines a high safety of operation and lack of susceptibility to malfunctioning with very good cleanability. Improved manufacturing conditions, in particular in relation to pharmaceutical and hygiene requirements on change of product, are thus created.

EXAMPLES

The invention is illustrated by means of specific examples of use without being restricted in any way thereby.

Example 1

An ibuprofen melt with a temperature of 110° C. was sprayed into an apparatus which is characterized by the configuration described above. The processing chamber is characterized by a rectangular cross section and has a cross-sectional area of $0.15 \times 0.2 = 0.03$ m$^2$ and a height of about 1 m above the inclined side walls. The process air stream which is preheated to about 40° C. is supplied at about 150 m$^3$/h through 2 gas supply slits running lengthwise through the apparatus. The melt was sprayed in through a two-fluid nozzle spraying vertically upwards and fed with compressed air into the process air jet with a mass flow rate of about 30 g/min. The spraying air was heated to 90° C. About 500 g of ibuprofen granules were present in the processing chamber. Dust was removed from the exit air by a cyclone downstream of the apparatus, and the deposited solid was fed gravimetrically into the process chamber in the vicinity of the slit as nucleus material. A zig-zag classifier was used to remove granules continuously from the front of the processing chamber. The fines separated in the classifier were blown back by the screening air into the processing chamber. The removed granules have a usual uncompacted apparent density and a usual particle size distribution and are thus suitable for further processing. Thus, the following particle size distribution was found (sieve analysis):
>400 µm: 0.8 mass %
315 ... 400 µm: 6.8 mass %
250 ... 315 µm: 15.3 mass %
160 ... 250 µm: 42.3 mass %
100 ... 160 µm: 24.9 mass %
0 ... 100 µm: 9.9 mass %

Example 2

An ibuprofen melt with a temperature of 110° C. was sprayed into an apparatus which is characterized by the configuration described above. The processing chamber is characterized by a rectangular cross section and has a cross-sectional area of 0.2×1.0=0.2 m² and a height of about 1 m above the inclined side walls. The process air stream which is preheated to about 45° C. was supplied at about 780 m³/h through 2 gas supply slits running lengthwise through the apparatus. The entire process air flow was uniformly distributed to 4 inlet air chambers of equal size. The previously described processing chamber extents at the upper part along the inlet air chambers and is not subdivided. The melt was sprayed through two two-fluid nozzles supplied with compressed air and spraying vertically upwards into the process air jet at a total mass flow rate of about 22 kg/h. About 6 kg of ibuprofen granules were present in the processing chamber. Dust was removed from the exit air by a cartridge filter which was integrated in the apparatus and was cleaned cyclically by pulses of compressed air. The unclassified removal of granules from the processing chamber took place at the front using a star wheel discharger. The complete discharged stream of granules was then guided into a screening system where an oversized portion (>400 µm) and an undersized portion (<200 µm) were screened off. The undersized portions removed in the screen were blown back pneumatically into the processing chamber. The oversized material was continuously ground in a pinned disc mill and likewise conveyed back as granulation nuclei into the processing chamber. The removed granules (>200 µm and <400 µm) also have in this case an adequate uncompacted bulk density which is suitable for further processing, and adequate particle size distribution which is detailed below:
>400 µm: 0.8 mass %
315 ... 400 µm: 6.8 mass %
250 ... 315 µm 15.3 mass %
160 ... 250 µm: 42.3 mass %
100 ... 160 µm: 24.9 mass %
1.00 µm 9.9 mass %

REFERENCE NUMBERS

1 Slit aperture(s)
2 Gas jet(s)
3 Deflecting part
4 Discharge element
5 Side wall
6 Spray nozzle(s) spraying in any directions
7 Spray nozzle(s) spraying upwards
8 Processing chamber
9 Cross section of a process stage
10 Process gas
11 Exit gas
12 Insulator with cooling or heating system
13 Input system
14 Expansion zone
15 Solid circulation
16 Guide plate(s)
17 Inlet air chamber
18 Pulses of compressed air
19 Exit-air part
20 Solid-loaded exit air
21 Removed and returned solid.
22 Nozzle-spraying zone
23 Particle exit from the gas jet
24 Return zone
25 Dust removal system
26 Feeds
27 Mechanical comminuting units
28 Heat-transfer units
29 Side wall

The invention claimed is:
1. A method for producing particles with length-width ratios of a largest particle dimension to a smallest particle dimension which is fixed at an angle of 90° in relation to the largest particle dimension in a range of from 1.0 to less than about 1.4 from a pharmaceutical substance, the method comprising the following stages:
(a) providing a melt of the pharmaceutical substance;
(b) producing droplets of the melt by spraying the melt into a processing chamber in which a spouted bed of fluidized solid particles is formed;
(c) repeatedly guiding solid particles of the pharmaceutical substance past the sprayed droplets in the processing chamber with the aid of a process gas jet which is guided in a defined way and which has a temperature that is fixed, depending on the solidification point of the melt, so that at least some of the droplets come into contact with particles and solidify thereon; and
(d) removing particles from the processing chamber as a function of the particle size;
wherein the temperature of the process gas jet which is guided in a defined way is 10° C. to 40° C. below the solidification point of the melt.
2. The method according to claim 1;
wherein the average particle size of the produced particles is in the range from 0.1 to 3 mm.
3. The method according to claim 1;
wherein the length-width ratios of the particles are in a range of from 1.0 to less than about 1.3.
4. The method according to claim 1;
wherein solid particles are guided past sprayed droplets by spraying droplets of the melt into the spouted bed.
5. The method according to claim 4;
wherein the droplets of the melt are sprayed into the spouted bed in a region of an ejection zone.
6. The method according to claim 5;
wherein the droplets are sprayed in the same direction as the process gas jet.
7. The method according to claim 5;
wherein the droplets are sprayed into the ejection zone in a region adjoining a return zone.
8. The method according to claim 1;
wherein the melt represents a homogeneous liquid phase.
9. The method according to claim 1;
wherein the melt comprises solid substances dispersed therein.

10. The method according to claim 1;
wherein solid particles are introduced into the processing chamber from outside.

11. The method according to claim 1;
wherein the pharmaceutical substance is an active pharmaceutical ingredient.

12. The method according to claim 11;
wherein the active pharmaceutical ingredient is ibuprofen.

13. The method according to claim 1, further comprising:
comminuting particles of the pharmaceutical substance within the processing chamber to reduce their size; and
guiding the comminuted particles past the sprayed droplets in the processing chamber with the aid of the process gas jet so that at least some of the droplets come into contact with the comminuted particles and solidify thereon.

* * * * *